United States Patent

Karlsson et al.

[11] Patent Number: 5,523,470
[45] Date of Patent: Jun. 4, 1996

[54] SURFACTANT, PROCESS FOR ITS PRODUCTION AND USE

[75] Inventors: Leif Karlsson, Stenungsund; Per-Erik Hellberg, Svenshögen; Lena Eriksson; Stig Svennberg, both of Stenungsund, all of Sweden; Eimund Gilje, Oltedal, Norway; Siri Espedal, Stavanger, Norway; Trygve Maldal, Røyneberg, Norway

[73] Assignees: Berol Nobel AB, Stenungsund, Sweden; Den norske stats oljeselskap a.s., Stavanger, Norway

[21] Appl. No.: 222,912

[22] Filed: Apr. 5, 1994

[30] Foreign Application Priority Data

Jun. 23, 1993 [NO] Norway ................... 932315

[51] Int. Cl.$^6$ .................................................. C07C 309/02
[52] U.S. Cl. ........................................................ 562/110
[58] Field of Search ........................ 554/96, 97; 562/110

[56] References Cited

U.S. PATENT DOCUMENTS

| | | | |
|---|---|---|---|
| 4,436,672 | 3/1984 | Naylor | 252/8.55 |
| 4,446,079 | 5/1984 | Hoskin | 252/8.55 D |
| 4,460,481 | 7/1984 | Schievelbein | 252/8.55 D |
| 4,466,891 | 8/1984 | McCoy | 252/8.55 D |
| 4,468,335 | 8/1984 | Chen et al. | 252/8.55 D |
| 4,468,342 | 8/1984 | Chen | 252/8.55 D |
| 4,515,701 | 5/1985 | Hoskin | 252/8.55 D |
| 4,540,049 | 9/1985 | Hawkins et al. | 252/8.55 D |
| 4,545,912 | 10/1985 | Schmitt | 252/8.55 D |
| 4,590,996 | 5/1986 | Hoskin et al. | 252/8.55 D |
| 4,603,009 | 7/1986 | Hoskin | 252/8.55 D |
| 4,733,728 | 3/1988 | Morita et al. | 252/8.55 D |
| 4,831,176 | 5/1989 | Holmberg et al. | 252/8.55 D |
| 4,979,564 | 12/1990 | Kalpakei et al. | 252/8.55 |

FOREIGN PATENT DOCUMENTS

| | | |
|---|---|---|
| 0088206 | 9/1983 | European Pat. Off. . |
| 161976 | 7/1989 | Norway . |
| 170411 | 7/1992 | Norway . |
| 170972 | 9/1992 | Norway . |
| 9115289 | 10/1991 | WIPO . |
| 9115290 | 10/1991 | WIPO . |

*Primary Examiner*—José G. Dees
*Assistant Examiner*—Joseph M. Conrad, III
*Attorney, Agent, or Firm*—Birch, Stewart, Kolasch & Birch

[57] ABSTRACT

A new class of surfactants exhibits properties, which make the surfactants suitable for use in surfactant flooding for enhanced oil recovery. The surfactants have the formula $$XA_rORSO_3^- M^+ \qquad (I)$$

where R is a hydrocarbon or hydroxyl-substituted hydrocarbon group with 2–6 carbon atoms; A is an oxyalkylene group having 2–4 carbon atoms; r is a number from 0–10, preferably 0–5 and most preferably 1–4; X is an hydroxyl group or hydroxyl and ether group containing hydrophobic group, which comprises 2–6, preferably 2–4 end groups containing 3–22 carbon atoms; and M is a cation, preferably a monovalent cation; or a $C_{1-4}$-alkyl ether thereof. A method for the manufacture of the surfactants are also enclosed.

6 Claims, No Drawings

SURFACTANT, PROCESS FOR ITS PRODUCTION AND USE

The present invention relates to an anionic surfactant having a branched hydrophobic group containing at least two end groups with 3–22 carbon atoms. The surfactant is easy to prepare and forms microemulsions without a need of a cosurfactant. The surfactant and the microemulsion containing said surfactant are suitable for use in enhanced oil recovery.

One of the most interesting application areas for microemulsions is surfactant flooding for enhanced oil recovery. However, microemulsions normally do only exist within fairly narrow intervalls with regard to the surfactant to cosurfactant weight ratio.

The problem of component separation can be avoided or reduced by using certain branched surfactants which easily form microemulsions with or without the addition of a cosurfactant. For example, U.S. Pat. Nos. 4,468,335, 4,468,342, and 4,545,912 disclose surfactants with a branched hydrophobic tail and a polar group consisting of a polyethylene glycol chain with a terminal sulfonate group. These surfactants have been shown to form microemulsions also without a cosurfactant and they have a high capacity to solubilize oil and have been suggested for use in enhanced oil recovery. Still better properties are shown by the surfactant disclosed in U.S. Pat. No. 4,446,079 and the publications WO 91/15289 and WO 91/15290. Insertion of a nonionic hydrophilic group between the sulfate or the sulfonate end group and the 1,3-dialkoxypropyl hydrophobic tail gives these surfactants an excellent ability to solubilize oil in the microemulsion phase. Especially the surfactants in which the two alkyl groups in the dialkoxypropyl group have a different number of carbon atoms have proved to be very useful in surfactant flooding as they have a low sensitivity to variations in salinity, temperature and the alkaline carbon number of the oil. In practice such an insensitivity is necessary in large scale operation in off-shore flooding, since the conditions in the reservoir vary considerably.

However, the surfactants disclosed in U.S. Pat. No. 4,446,079, WO 91/15289 and WO 91/15290 have proved to be difficult and expensive to produce as the number of process steps and the total yield is rather low. These facts hamper the commercial use of the surfactants. There is therefore a need for a new surfactant which is easy to produce in a relatively high yield and have at least about the same high solubilizing effect and low sensitivity to variations in salinity, temperature and alkane carbon number of the oil as the surfactants disclosed in WO 91/15289 and WO 91/15290.

We have now surprisingly found that a new class of novel surfactants exhibits even improved solubilizing effect and tolerance to variations in the oil reservoir in comparison with the prior art. The surfactants are also comparatively easy to produce. They have a molecular weight of from 350–900, preferably from 400–750 and the formula $$XA_rORSO_3^- M^+ \quad (I)$$

where R is a hydrocarbon or hydroxyl-substituted hydrocarbon group with 2–6 carbon atoms; A is an oxyalkylene group having 2–4 carbon atoms; r is a number from 0–10, preferably 0–5 and most preferably 1–4; X is an hydroxyl or hydroxyl and ether containing hydrophobic group, which comprises 2–6, preferably 2–4 end groups containing 3–22 carbon atoms; and M is a cation, preferably a monovalent cation; or a $C_{1-4}$-alkyl ether thereof. The hydrophobic group X, which is dominated by hydrocarbon groups, contains at least one hydroxyl group and may also contain one or more ether groups. Although these groups are polar tests have shown that the presence of these groups also contribute to improved solubilizing effects. In order to facilitate the introduction of the sulphonate group the hydroxyl groups may be at least partially alkylated.

Suitable embodiments of surfactants with formula I are those where X has the formula $$H[(B)_mQ]_n- \quad (II)$$

in which B is an alkylene group having 2–4 carbon atoms; m is a number from 0–10, preferably 0–5, n is a number from 1–5, preferably 1–3, and Q is i) a group $-OCR_1R_2CR_3R_4-$, where one or two of the groups $R_1$, $R_2$, $R_3$ and $R_4$ are monovalent groups with 1–22 carbon atoms, preferably 1–16 carbon atoms; and the remaining groups $R_1$, $R_2$, $R_3$ and $R_4$ are hydrogen, the total number of carbon atoms in the group $R_1$, $R_2$, $R_3$ and $R_4$ being from 3 to 22, preferably from 5–16, ii) the groups $-OCH(CH_2OR_5)CH_2-$, $-OCH_2CH(CH_2OR_5)-$ or $-OCH_2CH(OR_5)CH_2-$, where $R_5$ is a hydrocarbon group with 1–24, preferably 1–16 carbon atoms, or iii) the groups $$-OCHCH_2- \quad \text{or} \quad -OCH_2CH- $$
$$\quad | \qquad\qquad\qquad\qquad\qquad | $$
$$CH_2O(B)_m[Q(B)_m]_{n-1}H \qquad CH_2O(B)_m[Q(B)_m]_{n-1}H$$

where B, Q, m and n have the meaning mentioned above; or a $C_{1-4}$-alkyl ether, preferably a metyl ether thereof. Preferred surfactants of formula (II) are those, where A is an oxyethylene group and Q is the group $-OCR_1R_2CR_3R_4-$ containing 8–18 carbon atoms. Examples of suitable end groups are $R_1$, $R_2$, $R_3$ or $R_4$ groups with 5–16 carbon atoms such as hexyl, octyl, decyl, dodecyl, tetradecyl and hexadecyl; and hydrophobic polar groups $H(B)_m-$, such as $-C_3H_6OH$, $-C_4H_8OH$, $-(C_3H_6O)_2H$, $-(C_3H_6O)_3H$, $-(C_4H_8O)_2H$, $-C_3H_6OC_4H_8OH$, $-C_2H_4O(C_4H_8O)_2H$, $-(C_3H_6O)_2CH_3$, $-C_2H_4OC_4H_9$ and $-CH_2CH(OH)CH_2OC_2H_5$. Preferably the surfactant contains 1 or 2 alkyl groups and one polar group as end groups.

Example of especially suitable groups of surfactants within the formula (II) are $$H(B)_m-Q-(A)_rORSO_3^- M^+,$$

$$HQ-Q-(A)_rORSO_3^- M^+, \text{ or}$$

$$H(B)_m-Q-Q-(A)_rRSO_3^- M^+$$

in which formulae R, A, r, Q, B, m and M have the meaning mentioned above. Preferably m is a number from 2 to 4; Q is the group $OCHR_1CHR_3$, where at least one of $R_1$ and $R_3$ is an alkyl group having 3–16 carbon atoms and the remaining $R_1$ or $R_3$ group is hydrogen or an alkyl group having 1–2 carbon atoms; and B is oxypropyl.

The surfactant of the invention may easily be prepared by conventional chemical methods and obtained in high yields. A general method is as follows.

Step 1. One mole of phenol, an m-unsaturated alcohol having from 2 to 6 carbon atoms, such as vinyl alcohol, allyl alcohol or 3-butenol, or an alkylene oxide product thereof with 0–10 moles selected from the group of an alkylene oxide having 2–4 carbon atoms is reacted with 1–3 mole of an olefin epoxide having from 5 to 24 carbon atoms; glycidol; or an reaction product between epoxide formed from epichlorohydrin and an alcohol $R_5OH$, where $R_5$ has the meaning mentioned above.

Step 2. The reaction product from step 1 is further condensed with 0–10 moles selected from the group of a alkylene oxide having 2–4 carbon atoms.

Step 3. The reaction products from step 1 or step 2, if performed, is reacted with the epoxide, glycidol and epichlorohydrin reactants defined in step 1 and with alkylene oxides having 2–4 carbon atoms in amounts as defined in step 2 in 0–4 sequences.

Step 4. The hydroxyl groups of the reaction product from the preceding step may be at least partially alkylated with an $C_{1-4}$ alkyl group containing alkylation agent, such as dimetyl sulphate, metylchloride and ethylchloride.

Step 5. The reaction products from step 3 or step 4 if performed is sulfonated by a sulfonating agent, such as sodium bisulphite or sulfur trioxide.

Steps 1 to 3, carried out in the presence of a conventional catalyst, such as a Lewis acid in an amount of 0,2–5 per cent by weight. The reaction temperature is normally 60°–90° C. The alkylene oxide in step 1 is preferably ethylene oxide, while the alkylene oxide used in step 2 and 3 is preferably propylene oxide and/or butylene oxide or mixtures containing one or both of these alkylene oxide. Most preferred in these steps is propylene oxide. The preferred amount of the alkylene oxide in step 2 and 3 is 0–5 moles per equivalence of hydroxyl groups in the hydroxyl reactant and the amount of glycidol or epichlorohydrin reactant in step 1 and 3 is preferably 0–1 mole. When the amount of alkylene oxide is 0 mole, this represent the case when step 2 or the corresponding part in a sequence have been omitted.

A normal concentration of the surfactant in an aqueous solution ready for surfactant flooding is from 0.1–3% by weight. Preferably, the surfactants are used without any cosurfactants, but the use of additional surfactants and cosurfactants are also within the scope of this invention. In order to increase the solubility of the surfactants in the aqueous injection media, the surfactants could be added in the form of an inorganic or organic ammonium salt or combined with a solubilizing agent, such as a lower alcohol or a lower ethylene glycol monoalkyl ether.

In some cases, the use of mixtures of surfactants belonging the the present invention may be advantageously employed. Such mixtures may comprise two or more components with different meanings for, for instance, R, A, Q, B, r m and n. It is essential, however, that each component of such a mixture is useable alone, i.e. that it gives a middle phase microemulsion with oil and brine. By selecting one component which is a little bit too hydrophilic and one which is a little bit too hydrophobic, the mixture, which may be formulated to be at optimum, sometimes gives a larger middle phase microemulsion that could be obtained with one of the component only.

When performing chemical flooding operation the aqueous surfactant solution also commenly contains a polymer thickener and/or an aqueous solution containing the thickener is injected immediately after the injection of the aqueous surfactant solution. The thickener substantially increases the efficiency of the surfactant. Example of suitable thickeners are polysaccharides, such as xanthan gum; cellulose ethers, such as methyl cellulose, hydroxyethyl cellulose, hydroxypropyl hydroxyethyl cellulose and ethyl cellulose; unhydrolyzed or partially hydrolyzed polyacylamides; and starch and derivates thereof. Suitably the thickener is used in a content of 0.01–0.2% by weight.

The invention is further illustrated by the examples below.

EXAMPLE 1

One mole of allyl alcohol and 2 mole of ethylene oxide was reacted in the presence of 0,5% by weight of $SnCl_4$ at 70° C. When the reaction was completed the amount of $SnCl_4$ was increased to 1,5% by weight and 1 mole of a $C_{12}$ α-epoxide was added dropwise to the reaction mixture. After completion of the reaction 1 mole of $C_8$ α-epoxide was added dropwise. The reaction temperature was kept at 85° C. The obtained reaction product was then mixed with tert butyl hydroperoxide (0,1 mole) and 2-propanol (3 mole). This mixture was added dropwise to a sulfite solution, containing 0,01 mole sodium bisulfite, 0,15 mole sodium sulfite and 0,05 mole of a previously made sulphonate in a mixture of water and 2-propanol (70:30 by volume). During the reaction the pH was kept constant at 7,2 by the addition of sodium bisulfite. The reaction temperature was between 20° to 40° C. The reaction product obtained may be illustrated with the formula

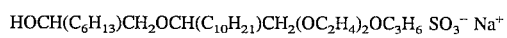
$HOCH(C_6H_{13})CH_2OCH(C_{10}H_{21})CH_2(OC_2H_4)_2OC_3H_6\ SO_3^-\ Na^+$ The structure was confirmed by following every reaction step by GC, NMR and/or GC-MS. The yield was about 81% by weight based on the allyl alcohol.

EXAMPLE 2

The process of Example 1 was repeated but the $C_8$ α-epoxide was replaced by $C_{12}$ α-epoxide. The reaction product obtained may be illustrated by the formula

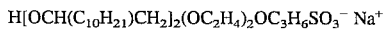
$H[OCH(C_{10}H_{21})CH_2]_2(OC_2H_4)_2OC_3H_6SO_3^-\ Na^+$

The structure was confirmed by following every reaction step by GC, NMR and/or GC-MS. The yield was about 80% by weight based on the allyl alcohol.

EXAMPLE 3

The process of Example 1 was repeated but the amount of ethylene oxide was 1,5 mole, the $C_{12}$ α-epoxide was replaced by 1,3 mole of $C_{16}$ α-epoxide and the $C_8$ α-epoxide was replaced by 2 moles of propylene oxide. The reaction product obtained may be illustrated with the formula

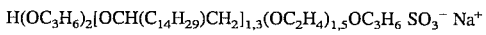
$H(OC_3H_6)_2[OCH(C_{14}H_{29})CH_2]_{1,3}(OC_2H_4)_{1,5}OC_3H_6\ SO_3^-\ Na^+$ The structure was confirmed by following every reaction step by GC, NMR and/or GC-MS. The yield was about 79% by weight based on the allyl alcohol.

EXAMPLE 4

The process of Example 1 was repeated but the amount of ethylene oxide was 1 mole, the amount of the $C_{12}$ α-epoxide was replaced by 1,3 mole of $C_{16}$ α-epoxide and the $C_8$ α-epoxide was replaced by 2 moles of propylene oxide. The reaction product may be illustrated by the formula

$H(OC_3H_6)_2[OCH(C_{14}H_{29})CH_2]_{1,6}OC_2H_4OC_3H_6\ SO_3^-\ Na^+$ The structure was confirmed by following every reaction step by GC, NMR and/or GC-MS. The yield was about 82% by weight based on the allyl alcohol.

EXAMPLE 5

The process of Example 1 was repeated but the amount of ethylene oxide was 4 moles and the $C_8$ α-epoxide was replaced by 1 mole of $C_{16}$ α-epoxide. The end product obtained may be illustrated by the formula HOCH($C_{14}H_{29}$)CHOCH($C_{10}H_{21}$)CH$_2$(OC$_2$H$_4$)$_4$OC$_3$H$_6$SO$_3^-$ Na$^+$ The structure was confirmed by following every reaction step by GC, NMR and/or GC-MS. The yield was about 78% by weight based on the allyl alcohol.

EXAMPLE 6

The surfactants of Examples 1–6 were tested and compared with a previously known flooding surfactant from Norwegan Patent No 170 972, surfactant 2, hereinafter referred to as Comparison.

The potential to increase the recovery of the oil with the different surfactants was determined by flooding experiments in Brentheimer sandstone cores from Germany. The Brentheimer cores have petro-physical properties which are very much the same as the sandstone in the oil reservoirs in the North Sea. Table 1 states the basic properties of the Brentheimer cores and the general flooding conditions.

TABLE 1

| Length | 30 cm |
|---|---|
| Diameter | 3,75 cm |
| Porosity | 23% |
| Permeability | 2000 mD |
| Over burden pressure | 30 bar |
| Pore pressure | 10 bar |
| Temperature | 50, 70 and 90° C. |

When testing the surfactants three different and typical crude oils from the North Sea as well as n-octane were used. The properties of the crude oils are stated in Table 2.

TABLE 2

| | Crude oil | | |
|---|---|---|---|
| Physical properties | A | B | C |
| Density, kg/m$^3$ | 820 | 882 | 662 |
| Viscosity, mPas | 0,34 | 1,11 | 0,41 |
| Gas/oil ratio, Sm$^3$/m$^3$ | 190 | 94 | 192 |
| Bubble point pressure, bar | 276 | 244 | 269 |
| | (95° C.) | (70° C.) | (100° C.) |

The Brentheimer cores were saturated with sea water and then placed in a core holder with an over burden pressure as stated above at 50°, 70° or 90° C. The cores were flooded in sequence with paraffin, high viscosity white oil, paraffin and crude oils finally with one of the A, B and C or with n-octane. The oil-saturated cores were then subjected to flooding with sea-water in a volume twice the pore volume of the core and the amount of oil recovered was measured.

The sea-water flooding was followed by flooding with 0,5 pore volume of sea-water containing 2% by weight of a surfactant and 1,5 pore volume of sea-water.

The additional amount of oil obtained in the surfactant flooding was determined as $$Rec(Sor) = \frac{Sor - Sorc}{Sor} \times 100$$

where Sor is the remaining oil amount after sea-water flooding and Sorc is the remaining amount after surfactant flooding. The following results were obtained.

| Surfactant Example | Oil | Temperature °C. | Rec(Sor) % |
|---|---|---|---|
| 1 | B | 50 | 83 |
| 2 | Octane | 50 | 88 |
| 2 | B | 50 | 79 |
| 2 | B | 70 | 73 |
| 2 | B | 90 | 70 |
| 2 | C | 70 | 64 |
| 5 | C | 70 | 55 |
| 3 | A | 50 | 63 |
| 3 | B | 50 | 74 |
| 4 | A | 50 | 91 |
| 4 | B | 50 | 85 |
| Control | B | 50 | 78 |

The surfactant flooding with surfactants according to the invention results in high additional oil recoveries when used at different temperatures and on different crude oils. Tolerance for relatively large changes in temperatures and in properties of the crude oil is of essential importance as temperatures and crude oil quality varies within the oil fields.

Due to the large amounts of surfactants involved when performing chemical flooding it is of essential importance that ratio between the amount of oil recovered and the amount of surfactant added is high.

In order to determine the effect $$Eff = \frac{ml(oil)}{g(surf)}$$

where ml (oil) is additional oil recovered by surfactant flooding and g (surf) is the amount of the surfactant added trials were carried out on Brentheimer cores saturated with the oils A and B. After flooding with sea-water the cores were subjected to surfactant flooding with a surfactant sea-water solution containing a surfactant and 500 ppm of xanthan gum, followed by 0,5 pore volume of sea-water containing 500 ppm xanthan gum, and finally sea-water until no more oil was recovered.

The following results were obtained.

TABLE 4

| Surfactant solution | | | | | |
|---|---|---|---|---|---|
| Surfactant Example | Surfactant % by weight | Pore volume | Oil type | Temp °C. | Eff ml/g |
| *3 | 2 | 0,5 | A | 50 | 35 |
| *3 | 2 | 0,5 | B | 50 | 30 |
| 3 | 0,5 | 0,62 | A | 50 | 100 |
| 3 | 0,5 | 0,52 | B | 50 | 130 |
| 3 | 0,5 | 0,26 | B | 50 | 180 |
| 3 | 0,5 | 0,26 | B | 70 | 120 |
| *4 | 2 | 0,5 | A | 50 | 38 |
| *4 | 2 | 0,5 | B | 50 | 36 |
| 4 | 0,5 | 0,48 | A | 50 | 130 |
| 4 | 0,5 | 0,26 | A | 50 | 140 |
| 4 | 0,5 | 0,48 | B | 50 | 145 |
| 4 | 0,5 | 0,28 | B | 50 | 150 |
| 4 | 0,7 | 0,26 | B | 50 | 140 |
| 4 | 1,0 | 0,26 | B | 50 | 145 |
| 4 | 0,5 | 0,43 | B | 40 | 140 |
| 4 | 0,5 | 0,26 | B | 70 | 110 |
| Control | 0,5 | 0,73 | B | 50 | 51 |

*Xanthan gum has not been added.

The results show that the surfactants in accordance with present invention, especially in combination with a polymer release a large amount of oil in relationship to the amount added. It is also evident that the surfactants according to the invention are superior to the Control.

We claim:

1. A surfactant or a $C_1$–$C_4$ alkyl ether thereof having the formula $$XA_rORSO_3^- \ M^+ \qquad (I)$$

where R is a hydrocarbon or hydroxyl-substituted hydrocarbon group having 2–6 carbon atoms; A is an oxyalkylene group having 2–4 carbon atoms; r is an integer from 0–10; X is a hydrophobic group having at least one hydroxyl group or a hydrophobic group having at least one hydroxyl group and at least one ether group, said hydrophobic group having 2–6 end groups containing 3–22 carbon atoms; and M is a cation; said surfactant having a molecular weight of from 350–900.

2. The surfactant according to claim 1, wherein X is a hydrophobic group having at least one hydroxyl group and one or more ether groups.

3. The surfactant according to claim 1, wherein the end groups in X are monovalent groups having a total number of 5–16 carbon atoms, or a hydrophobic polar group —$(B)_mH$, where B is an oxyalkylene group having 2–4 carbon atoms and m is an integer from 0–10.

4. The surfactant according to claim 1 having the formula $$H(B)_m\text{—}Q\text{—}(A)_rORSO_3^- \ M^+,$$

$$HQ\text{—}Q\text{—}(A)_rORSO_3^- \ M^+, \text{ or}$$

$$H(B)_m\text{—}Q\text{—}Q\text{—}(A)_rORSO_3^- \ M^+$$

where R, A, r and M have the meaning mentioned above, B is an oxyalkylene group having 2–4 carbon atoms, m is an integer from 0–10 and Q is (i) a group —$OCR_1R_2CR_3R_4$—, where one or two of the groups $R_1$, $R_2$, $R_3$ and $R_4$ are monovalent groups having 1–22 carbon atoms; and the remaining groups $R_1$, $R_2$, $R_3$ and $R_4$ are hydrogen, the total number of carbon atoms in the group $R_1$, $R_2$, $R_3$ and $R_4$ being from 3 to 22, ii) the groups —$OCH(CH_2OR_5)CH_2$—, —$OCH_2CH(CH_2OR_5)$— or —$OCH_2CH(OR_5)CH_2$—, where $R_5$ is a hydrocarbon group having 1–24 carbon atoms, or iii) the groups

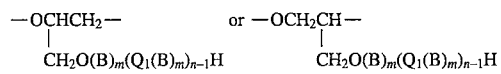

where B and m have the meaning mentioned above; n is an integer from 1–5 and $Q_1$ is i) a group —$OCR_1R_2CR_3R_4$—, where one or two of the groups $R_1$, $R_2$, $R_3$ and $R_4$ are monovalent groups having 1–22 carbon atoms; and the remaining groups $R_1$, $R_2$, $R_3$ and $R_4$ are hydrogen, the total number of carbon atoms in the group $R_1$, $R_2$, $R_3$ and $R_4$ being from 3 to 22, or ii) the groups —$OCH(CH_2OR_5)CH_2$—, —$OCH_2CH(CH_2OR_5)$— or —$OCH_2CH(OR_5)CH_2$—, where $R_5$ is a hydrocarbon group having 1–24 carbon atoms.

5. The surfactant according to claim 4, wherein m is an integer from 2 to 4; Q is a $OCHR_1CHR_3$ group, where at least one of $R_1$ and $R_3$ is an alkyl group having 3–16 carbon atoms and the remaining $R_1$ or $R_3$ group is hydrogen or an alkyl group having 1–2 carbon atoms; and B is oxypropyl.

6. The surfactant according to claim 1 or 2, wherein X has the formula $$H((B)_mQ)_n\text{—} \qquad (II)$$

where B is an oxyalkylene group having 2–4 carbon atoms; m is an integer from 0–10, n is an integer from 1–5, and Q is i) a group —$OCR_1R_2CR_3R_4$—, where one or two of the groups $R_1$, $R_2$, $R_3$ and $R_4$ are monovalent groups having 1–22 carbon atoms; and the remaining groups $R_1$, $R_2$, $R_3$ and $R_4$ are hydrogen, the total number of carbon atoms in the group $R_1$, $R_2$, $R_3$ and $R_4$ being from 3 to 22, ii) the groups —$OCH(CH_2OR_5)CH_2$—, —$OCH_2CH(CH_2OR_5)$— or —$OCH_2CH(OR_5)CH_2$—, where $R_5$ is a hydrocarbon group having 1–24 carbon atoms, or iii) the groups

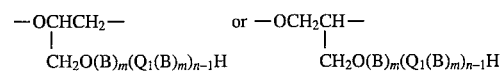

where B, m and n have the meaning mentioned above and $Q_1$ is i) a group —$OCR_1R_2CR_3R_4$—, where one or two of the groups $R_1$, $R_2$, $R_3$ and $R_4$ are monovalent groups having 1–22 carbon atoms; and the remaining groups $R_1$, $R_2$, $R_3$ and $R_4$ are hydrogen, the total number of carbon atoms in the group $R_1$, $R_2$, $R_3$ and $R_4$ being from 3 to 22, or ii) the groups —$OCH(CH_2OR_5)CH_2$—, —$OCH_2CH(CH_2OR_5)$— or —$OCH_2CH(OR_5)CH_2$—, where $R_5$ is a hydrocarbon group having 1–24 carbon atoms.

* * * * *